US009221039B2

(12) United States Patent
Lin et al.

(10) Patent No.: US 9,221,039 B2
(45) Date of Patent: Dec. 29, 2015

(54) CATALYST AND THE PREPARATION PROCESS THEREOF AND A PROCESS FOR EPOXIDISING OLEFIN

(75) Inventors: Min Lin, Beijing (CN); Hua Li, Yueyang (CN); Wei Wang, Yueyang (CN); Chijian He, Yueyang (CN); Xiaoju Wu, Yueyang (CN); Jizao Gao, Yueyang (CN); Xichun She, Yueyang (CN); Jun Long, Beijing (CN); Qingling Chen, Yueyang (CN)

(73) Assignees: China Petroleum & Chemical Corporation, Beijing (CN); Hunan Changling Petrochemical Science and Technology Development Co., Ltd., Yueyang (CN); Research Institute of Petroleum Processing, Sinopec, Beijing (CN)

( * ) Notice: Subject to any disclaimer, the term of this patent is extended or adjusted under 35 U.S.C. 154(b) by 357 days.

(21) Appl. No.: 13/878,662

(22) PCT Filed: Oct. 11, 2011

(86) PCT No.: PCT/CN2011/001701
§ 371 (c)(1),
(2), (4) Date: Jun. 3, 2013

(87) PCT Pub. No.: WO2012/048527
PCT Pub. Date: Apr. 19, 2012

(65) Prior Publication Data
US 2013/0253208 A1 Sep. 26, 2013

(30) Foreign Application Priority Data
Oct. 11, 2010 (CN) .......................... 2010 1 0511572

(51) Int. Cl.
*B01J 29/89* (2006.01)
*C07D 301/12* (2006.01)
*B01J 35/00* (2006.01)

(52) U.S. Cl.
CPC ................ *B01J 29/89* (2013.01); *B01J 35/002* (2013.01); *C07D 301/12* (2013.01); *B01J 2229/32* (2013.01); *B01J 2229/34* (2013.01); *B01J 2229/42* (2013.01)

(58) Field of Classification Search
CPC C07D 301/12; B01J 2229/32; B01J 2229/34; B01J 2229/42; B01J 35/002; B01J 29/89
See application file for complete search history.

(56) References Cited

U.S. PATENT DOCUMENTS

| | | | | |
|---|---|---|---|---|
| 5,082,641 | A * | 1/1992 | Popa et al. | 423/326 |
| 5,756,778 | A * | 5/1998 | Thiele et al. | 549/531 |
| 6,008,389 | A | 12/1999 | Grosch et al. | |
| 6,491,861 | B1 | 12/2002 | Grosch et al. | |
| 6,740,764 | B1 | 5/2004 | Chen et al. | |
| 7,563,740 | B2 | 7/2009 | Kaminsky et al. | |
| 2010/0022786 | A1 * | 1/2010 | Kawabata | 549/531 |
| 2013/0253208 | A1 * | 9/2013 | Lin et al. | 549/531 |
| 2014/0243538 | A1 * | 8/2014 | Crampton | 549/563 |

FOREIGN PATENT DOCUMENTS

| | | |
|---|---|---|
| CN | 1131152 A | 9/1996 |
| CN | 1132699 C | 12/2003 |
| CN | 101172970 A | 5/2008 |
| CN | 101274922 A | 10/2008 |
| EP | 1 110 910 A1 | 6/2001 |
| JP | 2000-511818 | 9/2000 |
| JP | 2001-524379 | 12/2001 |
| JP | 2002-504013 | 2/2002 |
| JP | 2010-513016 | 4/2010 |

OTHER PUBLICATIONS

International Search Report dated Jan. 19, 2012 issued in International Application No. PCT/CN2011/001701.
Extended European Search Report mailed Apr. 23, 2014, for European Application No. 11831924.3, (4 pages).

* cited by examiner

*Primary Examiner* — Timothy Vanoy
(74) *Attorney, Agent, or Firm* — Finnegan, Henderson, Farabow, Garrett & Dunner, LLP

(57) ABSTRACT

Disclosed herein are a catalyst, a preparation process thereof, and a process of epoxidizing olefin using the catalyst. The catalyst contains a binder and a titanium silicate as specified. The catalyst disclosed herein has high strength, and shows high catalytic activity in the epoxidation of olefins.

18 Claims, No Drawings

CATALYST AND THE PREPARATION PROCESS THEREOF AND A PROCESS FOR EPOXIDISING OLEFIN

This application is a U.S. National Stage under 35 U.S.C. §371 of international application PCT/CN2011/001701, which was filed on Oct. 11, 2011, claiming priority to Chinese Patent Application No. 201010511572.8, filed on Oct. 11, 2010.

TECHNICAL FIELD

The present invention relates to a catalyst and the preparation process thereof and a process for epoxidising olefin using the catalyst.

BACKGROUND

As the development of petrochemical industry and fine chemicals, the oxygen-containing organic compound has become a very important intermediate. The epoxidation of olefin using hydrogen peroxide as an oxidizer and using a titanium silicate as the catalyst to prepare an oxygen-containing organic compound satisfies the requirement of green chemistry and the developing idea of atom economy, and thus is a new green technology with great prospect.

Epoxides are generally prepared by the epoxidation of an olefin and hydrogen peroxide in the presence of a catalyst. Currently, the titanium silicate molecular sieves are the most popular catalysts. However, when a fixed bed process is used, the catalyst containing a titanium silicate must be shaped and have sufficient crushing strength; otherwise, the catalyst is ready to crush during use to form fine particles or powder. The crushed catalyst on one hand can result in increased pressure drop of the catalyst bed, so as to increase the production cost and also increase the production danger; on the other hand, if the crushed catalyst is carried over by the reaction product, it will result in the lose of catalyst and complex separation of products.

In order to increase the crushing strength of the catalyst, the conventional shaping of titanium silicate molecular sieves increases the catalyst strength depending mainly on increasing the amount of the binder. However, the increased amount of the binder will necessarily result in decreased content of the titanium silicate in the catalyst, namely decreasing the effective active component per unit weight of catalyst, so as to decrease the activity of the catalyst, which in turn decreases the availability of the reactor and increases the equipment cost and the operation cost.

CN101274922A discloses a process of preparing propylene oxide, which process prepares propylene oxide by the epoxidation of propylene using hydrogen peroxide as the oxidizer in the presence of a solvent; wherein the active component of the catalyst used by the process is a titanium silicate having a MFI structure. The crystal grain of the titanium silicate has a hollow structure, with a radial length of 5-300 nm for the cavity portion of the hollow grain. The adsorption capacity of benzene measured for the molecular sieve sample under the conditions of 25 degrees C., $P/P_0=0.10$ and 1 h of adsorption time is at least 70 mg/g, and there is a hysteresis loop between the adsorption isotherm and the desorption isotherm for nitrogen adsorption by the molecular sieve at a low temperature. However, the mass fraction of the titanium silicate in the catalyst used by the patent is 70%, and the selectivity for propylene oxide is only 72.5%. Therefore, the activity of the catalyst used in the process of preparing propylene oxide disclosed by the patent needs to be further increased.

U.S. Pat. No. 6,740,764B1 discloses a process of epoxidising olefin, comprising catalyzing the epoxidation of propylene and hydrogen peroxide using a catalyst containing a titanium silicate and an amorphous silica bonded to said titanium silicate molecular sieve. The patent discloses that a material containing at least elements Si and Ti and a crystalline silicate phase can be reacted with a silane and/or a silane derivative, so as to join together the amorphous silica and the crystalline silicate phase via a chemical bond; however, by calculation of the ratio between the titanium silicate and tetramethoxyl silane charged in the Examples disclosed by the patent, it can be seen that even if tetramethoxyl silane hydrolyzes completely, the content of amorphous silica in the finally obtained catalyst is about only 20 wt % (namely, with too high content of the binder).

In summary, it is still a problem to be solved about how to increase the content of molecular sieve in the catalyst as highly as possible to increase the catalytic activity of the catalyst, provided that the sufficient crushing strength of the catalyst is ensured.

SUMMARY OF THE INVENTION

The object of the present invention is to solve the problem in the prior art which cannot result in high content of molecular sieve in the catalyst with the proviso of ensuring the sufficient crushing strength of the catalyst for a catalyst using the titanium silicate as the active component. The present invention thus provides a titanium silicate catalyst having sufficient crushing strength and super high content of the molecular sieve, and the preparation process thereof.

The present invention provides a catalyst containing a binder and a titanium silicate molecular sieve, said binder being an amorphous silica, said titanium silicate having a MFI structure, and the crystal grain of said titanium silicate having a hollow structure, with a radial length of 5-300 nm for the cavity portion of the hollow structure, wherein the adsorption capacity of benzene measured for the titanium silicate under the conditions of 25 degrees C., $P/P_0=0.10$ and 1 h of adsorption time is at least 70 mg/g, and there is a hysteresis loop between the adsorption isotherm and the desorption isotherm for nitrogen adsorption by the molecular sieve at a low temperature; and wherein based on the total amount of the catalyst, the content of said binder is 3-15 wt %, the content of said titanium silicate is higher than 85-97 wt %; and said catalyst has a crushing strength value of not less than 60 N/cm measured according to GB3635-1983 standard method.

The present invention also provides a process for preparing said catalyst, comprising shaping a mixture to obtain a shaped article, heat-treating said shaped article in the presence of an aqueous base solution, drying and calcinating to obtain said catalyst, wherein said mixture contains a titanium silicate molecular sieve, a binder source and water, said titanium silicate having a MFI structure, and the crystal grain of said titanium silicate having a hollow structure, with a radial length of 5-300 nm for the cavity portion of the hollow structure, wherein the adsorption capacity of benzene measured for the molecular sieve under the conditions of 25 degrees C., $P/P_0=0.10$ and 1 h of adsorption time is at least 70 mg/g, and there is a hysteresis loop between the adsorption isotherm and the desorption isotherm for nitrogen adsorption by the molecular sieve at a low temperature; and wherein said binder source contains a silane and/or siloxane having at least two hydrolyzable groups.

The present inventors have found surprisingly that when using the hollow titanium silicate according to the present invention as the active component, and using the organosilane and/or organosiloxane having at least two hydrolyzable groups as at least a part of the binder source, even if the content of the molecular sieve in the catalyst is as high as 90 wt % or more, the catalyst obtained still has high enough crushing strength. For example, the crushing strength value measured according to GB3635-1983 standard method is not less than 60 N/cm, especially not less than 70 N/cm, particularly not less than 80 N/cm, more particularly not less than 100 N/cm, especially not less than 120 N/cm. As compared, when using a conventional non-hollow titanium silicate as the active component, even if the content of the molecular sieve in the catalyst is only 85 wt %, the catalyst obtained has very poor crushing strength, not satisfying the industrial requirement; and when the content of molecular sieve exceeds 90 wt %, no shaped catalyst can be obtained at all. The reason may be that the hollow titanium silicate has probably higher specific surface area and more surface silicon hydroxyl than the conventional titanium silicate molecular sieve, which is favorable for the silicon binder, especially the organosilane or organosiloxane, to chemically bond to the hydroxyl group on surface of the molecular sieve, so as to bind the titanium silicate molecular sieves together better, such that even if the content of molecular sieve is very high, the catalyst obtained still has high enough crushing strength. Owing to the super high content of molecular sieve, the catalyst provided by the present invention can increase the conversion of hydrogen peroxide while ensuring high selectivity for epoxides, or alternatively have high selectivity for epoxidised products while having high activity, when it is used for the epoxidation of an olefin.

EMBODIMENTS

The present invention provides a catalyst containing a binder and a titanium silicate molecular sieve, said binder being an amorphous silica, said titanium silicate having a MFI structure, and the crystal grain of said titanium silicate having a hollow structure, with a radial length of 5-300 nm for the cavity portion of the hollow structure, wherein the adsorption capacity of benzene measured for the titanium silicate under the conditions of 25 degrees C., $P/P_0=0.10$ and 1 h of adsorption time is at least 70 mg/g, and there is a hysteresis loop between the adsorption isotherm and the desorption isotherm for nitrogen adsorption by the molecular sieve at a low temperature; and wherein based on the total amount of the catalyst, the content of said binder is 3-15 wt %, particularly 4-15 wt %, especially 4-12 wt %, more particularly 4-9 wt % and especially 5-9 wt %, and the content of said titanium silicate is higher than 85-97 wt %, especially 88-96 wt %, particularly 91-96 wt %; and said catalyst has a crushing strength value of not less than 60 N/cm measured according to GB3635-1983 standard method.

In the catalyst according to the present invention, said titanium silicate is a hollow titanium silicate having a MFI structure. The crystal grain of said titanium silicate having said MFI structure has a hollow structure, with a radial length of 5-300 nm for the cavity portion of the hollow grain, wherein the adsorption capacity of benzene measured for the titanium silicate under the conditions of 25 degrees C., $P/P_0=0.10$ and 1 h of adsorption time is at least 70 mg/g, and there is a hysteresis loop between the adsorption isotherm and the desorption isotherm for nitrogen adsorption by the molecular sieve at a low temperature.

When an olefin is epoxidised in the presence of said hollow titanium silicate having a MFI structure, the reaction raw materials and solvent can enter the cavity portion of said catalyst easily to contact and react with the active component of the titanium silicate molecular sieve, so as to further enhance the reactivity of the catalyst. Meanwhile, the oxyalkylene as a product of the epoxidation can also fall off the active sites of the titanium silicate easily, in turn diffuse into the cavity of the titanium silicate molecular sieve, so as to reduce the residence time of the oxyalkylene at the active sites on the titanium silicate molecular sieve, and reduce the probability of side reactions of the oxyalkylene, such that the selectivity of the epoxidation is increased.

The hollow titanium silicate can be prepared referring to the process disclosed by CN1132699C, or can be obtained commercially. The hollow titanium silicate used in the Examples of the present invention is a hollow titanium silicate under the trademark of HTS manufactured by Hunan Jianchang Co. Ltd., China.

The catalyst according to the present invention further contains a binder, which binder is an amorphous silica. Said binder not only can endue said titanium silicate with certain shape, but also can make said catalyst have high strength. The amorphous silica can be chosen from various of non-crystalline silica generally used in the art, without particular limitation.

The catalyst according to the present invention comprises 3-15 wt % of said binder and 85-97 wt % of said titanium silicate molecular sieve, based on the total amount of the catalyst. A content of said titanium silicate within the above range not only can increase the activity of the catalyst, but also can ensure sufficient strength of the catalyst. In view of providing the catalyst with more balanced strength and catalytic activity, the content of said binder is preferably 3 wt % or more and less than 10 wt %, and the content of said titanium silicate is preferably higher than 90 wt % and not more than 97 wt %, based on the total amount of the catalyst. Most preferably, the content of said binder is 4-9 wt %, and the content of said titanium silicate is 91-96 wt %, based on the total amount of the catalyst.

The catalyst according to the present invention has a crushing strength of not less than 60 N/cm, preferably not less than 100 Ncm, more preferably not less than 120 N/cm, as measured according to GB3635-1983 standard method.

The catalyst according to the present invention can further comprise the oxide of an alkaline earth metal. Said oxide of the alkaline earth metal can neutralize the acidic sites of said catalyst, which in turn decreases the probability of side reactions by the epoxidation product, so as to increase the selectivity for the epoxidation product. Preferably, said metal oxide is a magnesia and/or a calcia.

When the catalyst according to the present invention further comprises the oxide of an alkaline earth metal, the content of said titanium silicate is 90-97 wt %, the total amount of the amorphous silica and the metal oxide is 3-10 wt %, and the weight ratio of the binder to the oxide of the alkaline earth metal is 1:(0.05-1), based on the total amount of the catalyst. In particular, the content of said titanium silicate is 90-97 wt %, the total amount of the amorphous silica and the metal oxide is 3-10 wt %, and the weight ratio of said amorphous silica to the oxide of the alkaline earth metal is 1:(0.1-0.3), based on the total amount of said catalyst. Further preferably, the content of said titanium silicate is 93-97 wt %, the total amount of the amorphous silica and the metal oxide is 3-7 wt %, and the weight ratio of said amorphous silica to the oxide of the alkaline earth metal is 1:(0.1-0.3), based on the total amount of said catalyst. The present invention also provides a process for preparing said catalyst, comprising shaping a mixture to obtain a shaped article, heat-treating said shaped article in the presence of an aqueous base solution, drying and calcinating to obtain said catalyst, wherein said mixture contains a titanium silicate molecular sieve, a binder source and water, said titanium silicate having a MFI structure, and the crystal grain of said titanium silicate having a hollow structure, with a radial length of 5-300 nm for the cavity portion of the hollow structure, wherein the adsorption capacity of benzene measured for the molecular sieve under the conditions of 25 degrees C., $P/P_0=0.10$ and 1 h of adsorption time is at least 70 mg/g, and there is a hysteresis loop between the adsorption isotherm and the desorption isotherm for nitrogen adsorption by the molecular sieve at a low temperature; and wherein said binder source contains a silane and/or siloxane having at least two hydrolyzable groups.

In the presence of water, said silane and/or siloxane having at least two hydrolyzable groups can on one hand react themselves via hydrolytic condensation to form amorphous silica, so as to bind the titanium silicate together. On the other hand, said silane and/or siloxane, or the amorphous silica formed can also condense with the surface hydroxyls of the titanium silicate molecular sieve, such that at least a part of the amorphous silica bond to said titanium silicate via chemical bonds, which in turn further increase the strength of the catalyst according to the present invention.

Said silane and/or siloxane having at least two hydrolyzable groups can be various silanes and/or siloxanes containing a hydrolyzable group in the molecular structure known to those skilled in the art.

Preferably, said silane containing at least two hydrolyzable groups is a silane of formula 1 below:

formula 1 wherein, at least two of $R_1$, $R_2$, $R_3$ and $R_4$ are each independently —$OR_{11}$ or —$OCOR_{12}$, at most two of $R_1$, $R_2$, $R_3$ and $R_4$ are each independently —$R_{13}$, $R_{11}$ and $R_{12}$ are each independently a linear or branched $C_1$-$C_5$ alkyl, and $R_{13}$ is a linear or branched $C_1$-$C_5$ alkyl.

More preferably, said silane having at least two hydrolyzable groups silane is one or more selected from the group consisting of tetramethoxyl silane, tetraethoxysilane, methyltrimethoxy silane, ethyltrimethoxy silane, dimethyldimethoxy silane, diethyldimethoxy silane, methyltriethoxy silane, dimethyldiethoxysilane, methyl metasilicate and ethyl metasilicate.

Preferably, said siloxane having at least two hydrolyzable groups is a siloxane of formula 2 below:

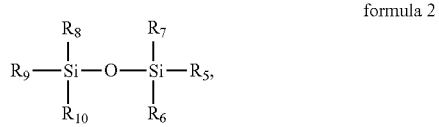

formula 2 wherein, at least two of $R_5$, $R_6$, $R_7$, $R_8$, $R_9$ and $R_{10}$ are each independently —$OR_{14}$ or —$OCOR_{15}$, at most four of $R_5$, $R_6$, $R_7$, $R_8$, $R_9$ and $R_{10}$ are each independently —$R_{16}$, $R_{14}$ and $R_{15}$ are each independently a linear or branched $C_1$-$C_5$ alkyl, and $R_{16}$ is a linear or branched $C_1$-$C_5$ alkyl.

In the present invention, the linear or branched $C_1$-$C_5$ alkyl can be methyl, ethyl, n-propyl, iso-propyl, n-butyl, iso-butyl, sec-butyl, t-butyl and n-pentyl.

More preferably, said siloxane having at least two hydrolyzable groups is 1,3-dimethoxy-1,1,3,3-tetramethyl disiloxane and/or 1,3-diethoxy-1,1,3,3-tetramethyl disiloxane.

The amounts of the titanium silicate molecular sieve, the silane and/or siloxane having at least two hydrolyzable groups and water can be determined according to the expected amounts of the titanium silicate and the binder in the catalyst, as long as the amounts of said titanium silicate molecular sieve, the silane and/or siloxane having at least two hydrolyzable groups and water are such that the contents of the titanium silicate and the binder in the final catalyst satisfy the requirement stated above. Namely, the content of the binder is 3-15 wt %, and the content of the titanium silicate is 85-97 wt %, based on the catalyst. Preferably, the content of said binder is 3 wt % or more and less than 10 wt %, and the content of said titanium silicate is higher than 90 wt % and not more than 97 wt %, based on the total amount of the catalyst. Most preferably, the content of said binder is 4-9 wt %, and the content of said titanium silicate is 91-96 wt %, based on the total amount of the catalyst.

In the process according to the present invention, the mixture can also comprise the oxide of an alkaline earth metal. The amount of the oxide of the alkaline earth metal in said mixture is such that the content of the alkaline earth metal in the finally prepared catalyst satisfies the requirement of specific applications (for example: the content ranges mentioned above). Preferably, in said mixture, the weight ratio among the titanium silicate molecular sieve, the binder source, the oxide of the alkaline earth metal and water is such that based on the total amount of the finally prepared catalyst, the content of said titanium silicate is 90-97 wt %, the total amount of the amorphous silica and the oxide of the alkaline earth metal is 3-10 wt %, and the weight ratio of said amorphous silica to the oxide of the alkaline earth metal is 1:(0.05-1). In particular, in said mixture, the weight ratio among the titanium silicate molecular sieve, the binder source, the oxide of the alkaline earth metal and water is such that based on the total amount of the finally prepared catalyst, the content of said titanium silicate is 90-97 wt %, the total amount of the amorphous silica and the metal oxide is 3-10 wt %, and the weight ratio of said amorphous silica to the oxide of the alkaline earth metal is 1:(0.1-0.3). More preferably, in said mixture, the weight ratio among the titanium silicate molecular sieve, the binder source, the oxide of the alkaline earth metal and water is such that based on the total amount of the finally prepared catalyst, the content of said titanium silicate is 93-97 wt %, the total amount of the amorphous silica and the metal oxide is 3-7 wt %, and the weight ratio of said amorphous silica to the oxide of the alkaline earth metal is 1:(0.1-0.3).

In the preparation process according to the present invention, the base can be either an organic base or an inorganic base. When said base is an inorganic base, it is preferably a base using an alkali metal as the cation; and when said base is an organic base, it is preferably a base capable of being degraded to release gas under the condition of a high temperature. Specifically, said base can be one or more selected from the group consisting of sodium hydroxide, potassium hydroxide, tetramethyl ammonium hydroxide and tetraethyl ammonium hydroxide. The amount of said base can be selected according to the amount of the silane and/or siloxane having at least two hydrolyzable groups. Preferably, the concentration of the aqueous base solution is 0.1-10 mol %, and the weight ratio of the aqueous base solution to the shaped article is (0.5-5):1.

Preferably, in the preparation process according to the present invention, the binder source further comprises a silica sol. Said silica sol preferably has a content of silica of 20-40 wt %. Preferably, calculated in silica, the weight ratio of the silica in said silica sol to the silane and/or siloxane having at least two hydrolyzable groups is 1:(0.02-1). A weight ratio of said silica sol to the silane and/or siloxane having at least two hydrolyzable groups falling into the range above not only can result in a catalyst with high strength, but also can decrease the content of the amorphous silica in the catalyst, so as to increase the activity of the catalyst.

In the preparation process according to the present invention, the thermal treatment not only hydrolytically condense the silane and/or siloxane having at least two hydrolyzable groups to form an at least a part of the amorphous silica, but also react at least a part of the amorphous silica with the surface hydroxyls of the titanium silicate molecular sieve. Thereby, a chemical bond is formed between at least a part of the amorphous silica and the titanium silicate molecular sieve, which enhances the interaction force therebetween, so as to bring higher strength to the finally prepared catalyst. The content of amorphous silica in the catalyst can be in turn decreased, and the quantity of active sites in unit weight of the catalyst is increased, such that the catalyst has higher catalytic activity.

The conditions for the thermal treatment according to the present invention are not particularly limited, as long as the conditions for the thermal treatment allow the silane and/or siloxane having at least two hydrolyzable groups to hydrolytically condense, and condense with the surface hydroxyls of the titanium silicate molecular sieve. Preferably, the conditions for the thermal treatment comprise: a temperature of 60-120 degrees C., and a duration of 2-15 hours.

In the preparation process according to the present invention, the mixture further comprises an auxiliary. The type of the auxiliary according to the present invention is not particularly limited, which can be various common auxiliaries in the art, preferably one or more selected from the group consisting of glycerol, polyvinylpyrrolidone, methyl cellulose and polyvinyl alcohol. The amount of said auxiliary can be determined based on the contents and types of the titanium silicate and the binder in said catalyst, as well as the strength and catalytic activity expected for the catalyst. Preferably, the amount of said auxiliary is 0.5-3 wt % based on the total amount of said mixture.

In the preparation process according to the present invention, the mixture further comprises a surfactant. The surfactant can decrease the surface tension of water significantly, such that the titanium silicate which is somewhat hydrophobic is ready to be wetted by water, which allows the amorphous silica to disperse on the titanium silicate more uniformly. The surfactant can be various surfactants known to those skilled in the art, without particular limitation.

The surfactant can be various water soluble surfactants and/or oil soluble surfactants known to those skilled in the art, without particular limitation. For example, said oil soluble surfactant can be a sorbitan aliphatic ester (Span series) and/or alkylphenol polyethenoxy ether (OP-10). Said oil soluble surfactant is preferably one or more selected from the group consisting of sorbitan mono-laurate (Span20), sorbitan mono-palmitate (Span40), sorbitan mono-stearate (Span60), sorbitan tri-stearate (Span65), sorbitan mono-oleate (Span80), sorbitan tri-oleate (Span85), nonylphenol polyethenoxy ether (TX-10), octylphenol polyethenoxy ether (OPE-10) and dodecylphenol polyethenoxy ether. Said water soluble surfactant can be such as one or more selected from the group consisting of a polyoxyethylene sorbitan aliphatic ester (Tween series), a polyoxyethylene aliphatic ester, a polyoxyethylene aliphatic alcohol ether (AEO series), polyoxyethylene-polyoxypropylene copolymer and alkylolamide (Ninol). Said water soluble surfactant is preferably one or more selected from the group consisting of polyoxyethylene sorbitan mono-laurate (Tween 20), polyoxyethylene sorbitan mono-palmitate (Tween 40), polyoxyethylene sorbitan mono-stearate (Tween 60), polyoxyethylene sorbitan mono-oleate (Tween 80) and polyoxyethylene sorbitan tri-oleate (Tween 85). The amount of said surfactant can be determined based on the amount and type of the titanium silicate and the amorphous silica used. Preferably, the amount of said surfactant is 0.001-0.2 wt % based on the total amount of said mixture.

The present invention also provides a process for epoxidising an olefin, comprising contacting the olefin with hydrogen peroxide in a solvent in a fixed bed reactor in the presence of a catalyst, wherein said catalyst is the catalyst provided by the present invention.

The catalyst according to the present invention for the epoxidation of olefin provides high conversion of hydrogen peroxide and selectivity for the epoxide, such that the process for epoxidising the olefin according to the present invention also provides high conversion of hydrogen peroxide and selectivity for the epoxide.

The process for epoxidising an olefin according to the present invention increases the conversion of hydrogen peroxide and the selectivity for epoxide by using the catalyst provided by the present invention, therefore, the other conditions for epoxidising the olefin in the present invention are not particularly limited, and various conditions known to those skilled in the art can be used to epoxidise the olefin, as long as the catalyst used is just the one provided by the present invention.

Preferably, the molar ratio of solvent:olefin:hydrogen peroxide is (4-15):(0.5-5):1. The olefin can be selected from the group consisting of olefins having 2-8 carbon atoms, for example: propylene, butylene and an isomer thereof, pentene and an isomer thereof, hexylene and an isomer thereof, heptylene and an isomer thereof, and octylene and an isomer thereof. Preferably, said olefin is propylene. The solvent can be selected from the group consisting of water, acetonitrile and an aliphatic alcohol having 1-6 carbon atoms. The examples of the aliphatic alcohol having 1-6 carbon atoms are: methanol, ethanol, propanol and an isomer thereof, butanol and an isomer thereof, pentanol and an isomer thereof, and hexanol and an isomer thereof. Preferably, said solvent is methanol. The conditions for contact are known to those skilled in the art. For example, the contact temperature can be 30-90 degrees C., the pressure can be 0.5-4.5 MPa, the pH of the reaction system can be 5-8, and the liquid hourly space velocity can be 0.1-7 h$^{-1}$. The liquid hourly space velocity involved in the present invention means a liquid hourly volume space velocity.

In the present invention, the amounts (weight, weight ratio or weight percentage) of solid matters including said titanium silicate molecular sieve, said oxide of the alkaline earth metal and said shaped article and others are calculated on the dry basis, wherein the so-called "dry basis" means the weight of a sample after a calcination at a temperature of 800 degrees C. for 2 hours.

The present invention will be illustrated in more detail below in combination with the Examples.

In the following examples, the crushing strength of catalysts is measured using a crushing strength detector with a model of QCY-602 (made by the Base-Making Institute of the Ministry of Chemical Industry), referring to the method specified by GB3635-1983.

The composition of the catalyst is measured by a X-Ray fluorescence spectrometer with a modal of Philips PW-2400, using X-Ray fluorescent spectrometry (XRF).

The composition of the epoxidation product is analyzed using gas chromatography:using methyl tert-butyl ether as the internal standard, using Agilent-6890 type chromatograph, using a FFTP capillary column with 30 m*0.25 mm, having a feeding amount of 1.0 μL and an inlet temperature of 180 degrees C. The temperature of the capillary column is kept at 60 degrees C. for 4 minutes, then raised to 200 degrees C. at a rate of 20 degrees C./minute, and kept for 4 minutes. A flame ionization detector (FID) is used. The temperature of the detecting chamber is 240 degrees C.

The conversion of hydrogen peroxide is calculated by the concentrations of hydrogen peroxide determined before and after the reaction using indirect iodometry.

Example 1

The example was provided to illustrate the catalyst for olefin epoxidation and the preparation process thereof and a process for epoxidising olefin using the catalyst according to the present invention.

100 g of titanium silicate powder (Hunan Jianchang Co., Ltd., under the trademark of HTS) was mixed homogeneously with 29.5 g of tetramethoxyl silane (Tsingtao Shijixing Chemical Reagent Co., Ltd.). After mixing, 20 g of silica sol (with 30 wt % of silica), 0.2 g of Span80, 2 g of polyvinyl alcohol (Sanming Dinghui Chemicals Co., Ltd., under the trademark of Polyvinyl Alcohol 2099), 1 g of sesbania powder (Zhuwa (Dongming County) Sesbania Gum Factory) and 50 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, the mixture was heated to 90 degrees C. and kept for 6 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 180 N/cm; and in the catalyst, the content of titanium silicate was 85 wt %, and the content of binder was 15 wt %, as measured by XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene:aqueous hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 $h^{-1}$. The reaction product was sampled and analyzed to show a conversion of hydrogen peroxide of 97.5%, and a selectivity for propylene oxide of 95.1%.

Comparative Example 1

A catalyst was prepared using a process same as example 1, except that the titanium silicate used was a conventional titanium silicate prepared referring to the process disclosed by document Thangaraj A, Kumar R, Mirajkar S P, et al. [J] J. Catal., 1991, 130(1):1-8. A measurement via XRF analysis showed that the content of titanium silicate in the catalyst was 85 wt %, the content of binder was 15 wt %, and the strength of the catalyst was 50 N/cm.

An epoxidation was conducted using a process same as example 1, except that the catalyst used was the one prepared by the comparative example 1. In the epoxidation, the conversion of hydrogen peroxide was 90.5%, and the selectivity for propylene oxide was 89.5%.

Comparative Example 2

100 g of titanium silicate powder (prepared according to the process disclosed by document Thangaraj A, Kumar R, Mirajkar S P, et al. [J] J. Catal., 1991, 130(1):1-8) was mixed homogeneously with 59 g of tetramethoxyl silane. After mixing, 30 g of silica sol (with 30 wt % of silica), 0.2 g of Span80, 2 g of polyvinyl alcohol (Sanming Dinghui Chemicals Co., Ltd., under the trademark of Polyvinyl Alcohol 2099), 1 g of sesbania powder (Zhuwa (Dongming County) Sesbania Gum Factory) and 60 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, and the mixture was heated to 90 degrees C. and kept for 6 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 180 N/cm; and in the catalyst, the content of titanium silicate was 75.5 wt %, and the content of binder was 24.5 wt %, as measured by XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene:aqueous hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 $h^{-1}$. The reaction product was sampled and analyzed to show a conversion of hydrogen peroxide of 85.5%, and a selectivity for propylene oxide of 89.2%.

Comparative Example 3

A catalyst was prepared using a process same as example 1, except that the amount of titanium silicate was 50 g. A measurement via XRF analysis showed that the content of titanium silicate in the catalyst was 73.9 wt %, the content of binder was 26.1 wt %, and the strength of the catalyst was 185 N/cm.

The epoxidation was conducted using a process same as example 1, except that the catalyst used was the one prepared by comparative example 3. In the epoxidation, the conversion of hydrogen peroxide was 91.7%, and the selectivity for propylene oxide was 94.5%.

Comparative Example 4

100 g of titanium silicate powder (Hunan Jianchang Co., Ltd., under the trademark of HTS) was mixed homogeneously with 58 g of silica sol (with 30 wt % of silica), which were then extruded, shaped and pelleted, followed by drying at 70 degrees C. for 4 hours. A shaped article with a dimension of 2*2 mm was obtained.

80 g of the shaped article above was calcinated at 550 degrees C. for 3 hours. It was found that the shaped article crushed, and no shaped article could be obtained.

Example 2

The example was provided to illustrate the catalyst for olefin epoxidation and the preparation process thereof and a process of epoxidising olefin using the catalyst according to the present invention.

100 g of titanium silicate powder (Hunan Jianchang Co., Ltd., under the trademark of HTS) was mixed homogeneously with 5 g of tetramethoxyl silane (Tsingtao Shijixing Chemical Reagent Co., Ltd.). After mixing, 11 g of silica sol (with 30 wt % of silica), 0.2 g of Span80, 2 g of polyvinyl alcohol (Sanming Dinghui Chemicals Co., Ltd., under the trademark of Polyvinyl Alcohol 2099), 1 g of sesbania powder (Zhuwa (Dongming County) Sesbania Gum Factory) and 50 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, and the mixture was heated to 120 degrees C. and kept for 2 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 160 N/cm; and in the catalyst, the content of titanium silicate was 97 wt %, and the content of binder was 3 wt %, as measured by XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene: aqueous hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 $h^{-1}$. The reaction product was sampled and analyzed to show a conversion of hydrogen peroxide of 99.8%, and a selectivity for propylene oxide of 95%.

Example 3

The example was provided to illustrate the catalyst for olefin epoxidation and the preparation process thereof and a process of epoxidising olefin using the catalyst according to the present invention.

100 g of titanium silicate powder (Hunan Jianchang Co., Ltd., under the trademark of HTS) was mixed homogeneously with 10 g of tetramethoxyl silane (Tsingtao Shijixing Chemical Reagent Co., Ltd.). After mixing, 19.9 g of silica sol (with 30 wt % of silica), 0.2 g of Span80, 2 g of polyvinyl alcohol (Sanming Dinghui Chemicals Co., Ltd., under the trademark of Polyvinyl Alcohol 2099), 1 g of sesbania powder (Zhuwa (Dongming County) Sesbania Gum Factory) and 50 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, and the mixture was heated to 60 degrees C. and kept for 15 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 180 N/cm; and in the catalyst, the content of titanium silicate was 91 wt %, and the content of binder was 9 wt %, as measured by XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene: aqueous hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 $h^{-1}$. The reaction product was sampled and analyzed to show a conversion of hydrogen peroxide of 98.1%, and a selectivity for propylene oxide of 95.3%.

Example 4

The example was provided to illustrate the catalyst for olefin epoxidation and the preparation process thereof and a process of epoxidising olefin using the catalyst according to the present invention.

100 g of titanium silicate powder (Hunan Jianchang Co., Ltd., under the trademark of HTS) was mixed homogeneously with 3 g of tetramethoxyl silane (Tsingtao Shijixing Chemical Reagent Co., Ltd.). After mixing, 10 g of silica sol (with 30 wt % of silica), 0.2 g of Span80, 2 g of polyvinyl alcohol (Sanming Dinghui Chemicals Co., Ltd., under the trademark of Polyvinyl Alcohol 2099), 1 g of sesbania powder (Zhuwa (Dongming County) Sesbania Gum Factory) and 60 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, and the mixture was heated to 90 degrees C. and kept for 6 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 180 N/cm; and in the catalyst, the content of titanium silicate was 96 wt %, and the content of binder was 4 wt %, as measured by XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene:aqueous hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 h$^{-1}$. The reaction product was sampled and analyzed to show a conversion of hydrogen peroxide of 99.2%, and a selectivity for propylene oxide of 94.9%.

Example 5

The example was provided to illustrate the catalyst for olefin epoxidation and the preparation process thereof and a process of epoxidising olefin using the catalyst according to the present invention.

100 g of titanium silicate powder (Hunan Jianchang Co., Ltd., under the trademark of HTS) was mixed homogeneously with 59.0 g of tetramethoxyl silane (Tsingtao Shijixing Chemical Reagent Co., Ltd.). After mixing, 0.2 g of Span80, 2 g of polyvinyl alcohol (Sanming Dinghui Chemicals Co., Ltd., under the trademark of Polyvinyl Alcohol 2099), 1 g of sesbania powder (Zhuwa (Dongming County) Sesbania Gum Factory) and 65 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, and the mixture was heated to 90 degrees C. and kept for 6 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 160 N/cm; and in the catalyst, the content of titanium silicate was 85 wt %, and the content of binder was 15 wt %, as measured by XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene:aqueous hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 h$^{-1}$. The reaction product was sampled and analyzed to show a conversion of hydrogen peroxide of 96.0%, and a selectivity for propylene oxide of 94.8%.

Example 6

The example was provided to illustrate the catalyst for olefin epoxidation and the preparation process thereof and a process of epoxidising olefin using the catalyst according to the present invention.

100 g of titanium silicate powder (Hunan Jianchang Co., Ltd., under the trademark of HTS) was mixed homogeneously with 40.3 g of tetraethoxy silane (Qufu Chenguang Chemicals Co., Ltd.). After mixing, 20 g of silica sol (with 30 wt % of silica), 2 g of polyvinyl alcohol (Sanming Dinghui Chemicals Co., Ltd., under the trademark of Polyvinyl Alcohol 2099), 1 g of sesbania powder (Zhuwa (Dongming County) Sesbania Gum Factory) and 50 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, and the mixture was heated to 90 degrees C. and kept for 6 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 150N/cm; and in the catalyst, the content of titanium silicate was 85 wt %, and the content of binder was 15 wt %, as measured by XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene:aqueous hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 h$^{-1}$. The reaction product was sampled and analyzed to show a conversion of hydrogen peroxide of 96.7%, and a selectivity for propylene oxide of 95.0%.

Example 7

The example was provided to illustrate the catalyst for olefin epoxidation and the preparation process thereof and a process of epoxidising olefin using the catalyst according to the present invention.

100 g of titanium silicate powder (Hunan Jianchang Co., Ltd., under the trademark of HTS) was mixed homogeneously with 41.1 g of 1,3-dimethoxy-1,1,3,3-tetramethyl disiloxane (commercially available from Advanced Technology Industry Co., Ltd.). After mixing, 20 g of silica sol (with 30 wt % of silica), 1 g of sesbania powder (Zhuwa (Dongming County) Sesbania Gum Factory) and 50 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, and the mixture was heated to 90 degrees C. and kept for 6 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 130 N/cm; and in the catalyst, the content of titanium silicate was 85 wt %, and the content of binder was 15 wt %, as measured by XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene:aqueous hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 $h^{-1}$. The reaction product was sampled and analyzed to show a conversion of hydrogen peroxide of 95.9%, and a selectivity for propylene oxide of 94.9%.

Example 8

The example was provided to illustrate the catalyst for olefin epoxidation and the preparation process thereof and a process of epoxidising olefin using the catalyst according to the present invention.

100 g of titanium silicate powder (Hunan Jianchang Co., Ltd., under the trademark of HTS) was mixed homogeneously with 1 g of magnesia and 10 g of tetramethoxyl silane (Tsingtao Shijixing Chemical Reagent Co., Ltd.). After mixing, 5 g of silica sol (with 30 wt % of silica), 0.2 g of Span80, 2 g of polyvinyl alcohol (Sanming Dinghui Chemicals Co., Ltd., under the trademark of Polyvinyl Alcohol 2099), 1 g of sesbania powder (Zhuwa (Dongming County) Sesbania Gum Factory) and 50 g of water were added and mixed homogeneously, which were then extruded, shaped and pelleted, followed by drying at 70 degrees C. for 4 hours. A shaped article with a dimension of 2*2 mm was obtained.

100 g of the shaped article above was placed into a 500 mL of three-necked flask, into which 200 g of 10 mol % aqueous sodium hydroxide solution was added, and the mixture was heated to 90 degrees C. and kept for 6 hours while stirring. A solid phase was then obtained by filtration, which solid phase obtained was washed by deionized water to be neutral. Then, the solid phase obtained was dried at 120 degrees C. for 3 hours, and finally calcinated at 550 degrees C. for 3 hours, so as to obtain the catalyst according to the present invention. A measurement showed that the strength of the catalyst was 160 N/cm; and in the catalyst, the content of titanium silicate was 93.2 wt %, the total content of the amorphous silica and magnesia was 6.8% weight, and the weight ratio of the amorphous silica to the magnesia was 1:0.2, as measured via XRF analysis.

14 g of the catalyst was loaded into the thermostatic reaction zone of a tubular fixed bed reactor, wherein ceramic ring packing was charged above and below the catalyst, and the entire reaction system was ensured to be well hermetic. The propylene and liquid streams were fed upward into the reaction zone, wherein the molar ratio of methanol:propylene:hydrogen peroxide in the liquid stream was 6:2:1, the liquid stream was added with aqueous ammonia to bring a pH of 5.3 to the liquid stream, while the liquid stream was added with 0.98 wt % of Span80 and 0.06 wt % of Tween 80. The reaction was controlled to have a temperature of 40 degrees C., a reaction pressure of 2.5 MPa, and a liquid hourly space velocity of 1.5 $h^{-1}$. The reaction product was sampled and analyzed to show a conversion of hydrogen peroxide of 98.5%, and a selectivity for propylene oxide of 97.7%.

Example 9

The example was provided to illustrate the catalyst for olefin epoxidation and the preparation process thereof and a process of epoxidising olefin using the catalyst according to the present invention.

A process same as example 8 was used to prepare the catalyst for olefin epoxidation except that the calcia was used in place of magnesia, the amount of titanium silicate powder (Hunan Jianchang Co., Ltd., under the trademark of HTS) was 120 g, the amount of calcia was 0.5 g, the amount of methyltriethoxy silane (Qufu Chenguang Chemicals Co., Ltd.) was 7 g, the amount of silica sol (with 30 wt % of silica) was 2 g, and the amount of Tween 20 was 0.15 g. A measurement showed that the strength of the catalyst was 120 N/cm; and in the catalyst, the content of titanium silicate was 97 wt %, the total content of the amorphous silica and calcia was 3% by weight, and the weight ratio of the amorphous silica to the calcia was 1:0.2, as measured via XRF analysis.

The epoxidation was conducted using a process same as example 1, except that the catalyst used was the one prepared by example 2. The reaction product was sampled and analyzed to show a conversion of hydrogen peroxide of 99.8%, and a selectivity for propylene oxide of 98.2%.

Table 1 summarized the content of titanium silicate in the catalyst, the crushing strength of the catalyst, as well as the conversion of the hydrogen peroxide and the selectivity for propylene oxide for the epoxidation according to examples 1-9 and comparative examples 1-4

TABLE 1

| | Content of titanium silicate (%) | Catalyst strength (N/cm) | Conversion of hydrogen peroxide (%) | Selectivity for propylene oxide (%) |
|---|---|---|---|---|
| Example 1 | 85 | 180 | 97.5 | 95.1 |
| Comparative example 1 | 85 | 50 | 90.5 | 89.5 |
| Comparative example 2 | 75.5 | 180 | 85.5 | 89.2 |
| Comparative example 3 | 73.9 | 185 | 91.7 | 94.5 |
| Comparative example 4 | — | — | — | — |
| Example 2 | 97 | 160 | 99.8 | 95.0 |
| Example 3 | 91 | 180 | 98.1 | 95.3 |
| Example 4 | 96 | 180 | 99.2 | 94.9 |
| Example 5 | 85 | 160 | 96.0 | 94.8 |
| Example 6 | 85 | 150 | 96.7 | 95.0 |
| Example 7 | 85 | 130 | 95.9 | 94.9 |

TABLE 1-continued

| | Content of titanium silicate (%) | Catalyst strength (N/cm) | Conversion of hydrogen peroxide (%) | Selectivity for propylene oxide (%) |
|---|---|---|---|---|
| Example 8 | 93.2 | 160 | 98.5 | 97.7 |
| Example 9 | 97 | 120 | 99.8 | 98.2 |

It could be seen from the comparison between example 1 and comparative example 1 that the catalyst using a hollow titanium silicate as the active component of the catalyst resulted in high conversion of the hydrogen peroxide and selectivity for propylene oxide, while having high strength.

It could be seen from the comparison between example 1 and comparative example 2 that under the same catalyst strengths, the catalyst according to the present invention not only had higher content of the titanium silicate molecular sieve, but also resulted in higher hydrogen peroxide conversion and propylene oxide selectivity in the epoxidation.

It could be seen from the comparison between example 1 and comparative example 3 that although they both used the titanium silicate with a hollow structure as the active component, the catalyst of example 1 had higher hydrogen peroxide conversion and propylene oxide selectivity owing to higher content of the titanium silicate molecular sieve.

It could be seen from the comparison between example 1 and comparative example 4 that if the binder source was completely the silica sol, the catalyst was hard to be shaped when the content of the titanium silicate was 85 wt %.

The invention claimed is:

1. A catalyst containing a binder and a titanium silicate, said binder being an amorphous silica, said titanium silicate having a MFI structure, and the crystal grain of said titanium silicate having a hollow structure, with a radial length of 5-300 nm for the cavity portion of the hollow structure, wherein the adsorption capacity of benzene measured for the titanium silicate under the conditions of 25 degrees C., $P/P_0=0.10$ and 1 h of adsorption time is at least 70 mg/g, and there is a hysteresis loop between the adsorption isotherm and the desorption isotherm for nitrogen adsorption by the molecular sieve at a low temperature; characterized in that based on the total amount of the catalyst, the content of said binder is 3-15 wt %, the content of said titanium silicate is 85-97 wt %; and said catalyst has a crushing strength value of not less than 60N/cm measured according to GB3635-1983 standard method.

2. The catalyst according to claim 1, wherein the content of said binder is 3 wt % or more and less than 10 wt %, the content of said titanium silicate is more than 90 wt % and not more than 97 wt %, based on the total amount of the catalyst.

3. The catalyst according to claim 2, wherein the content of said binder is 4-9 wt %, and the content of said titanium silicate is 91-96 wt %, based on the total amount of the catalyst.

4. The catalyst according to claim 1, wherein the catalyst further comprises an oxide of the alkaline earth metal, and the content of said titanium silicate is 90-97 wt %, the total amount of the binder and the metal oxide is 3-10 wt %, and the weight ratio of the binder to the oxide of the alkaline earth metal is 1:(0.05-1).

5. The catalyst according to claim 4, wherein the content of said titanium silicate is 93-97 wt %, the total amount of the binder and the metal oxide is 3-7 wt %, and the weight ratio of the binder to the oxide of the alkaline earth metal is 1:(0.1-0.3).

6. The catalyst according to claim 4, wherein the oxide of the alkaline earth metal is magnesia and/or calcia.

7. A process for preparing the catalyst according to claim 1, characterized in that the process comprises shaping a mixture to obtain a shaped article, heat-treating said shaped article in the presence of an aqueous base solution, drying and calcinating to obtain said catalyst, wherein said mixture contains a titanium silicate molecular sieve, a binder source and water, said titanium silicate having a MFI structure, and the crystal grain of said titanium silicate having a hollow structure, with a radial length of 5-300 nm for the cavity portion of the hollow structure, wherein the adsorption capacity of benzene measured for the titanium silicate under the conditions of 25 degrees C., $P/P_0=0.10$ and 1 h of adsorption time is at least 70 mg/g, and there is a hysteresis loop between the adsorption isotherm and the desorption isotherm for nitrogen adsorption by the molecular sieve at a low temperature; and wherein said binder source contains a silane and/or siloxane having at least two hydrolyzable groups.

8. The process according to claim 7, wherein the weight ratio among the titanium silicate molecular sieve, the binder source calculated in $SiO_2$ and water is (85-97):(3-15):(5-50).

9. The process according to claim 7, wherein the mixture further comprises an oxide of the alkaline earth metal, and in said mixture, the weight ratio among the titanium silicate molecular sieve, the binder source, the oxide of the alkaline earth metal and water is such that based on the total amount of the finally prepared catalyst, the content of said titanium silicate is 90-97 wt %, the total amount of the binder and the oxide of the alkaline earth metal is 3-10 wt %, and the weight ratio of the binder to the oxide of the alkaline earth metal is 1:(0.05-1).

10. The catalyst according to claim 9, wherein the content of said titanium silicate is 93-97 wt %, the total amount of the binder and the oxide of the alkaline earth metal is 3-7 wt %, and the weight ratio of the binder to the oxide of the alkaline earth metal is 1:(0.1-0.3), based on the total amount of the catalyst.

11. The process according to claim 7, wherein the silane having at least two hydrolyzable groups is a silane of formula 1,

formula 1 wherein, at least two of $R_1$, $R_2$, $R_3$ and $R_4$ are each independently $-OR_{11}$ or $-OCOR_{12}$, at most two of $R_1$, $R_2$, $R_3$ and $R_4$ are each independently $-R_{13}$, $R_{11}$ and $R_{12}$ are each independently a linear or branched $C_1$-$C_5$ alkyl, and $R_{13}$ is a linear or branched $C_1$-$C_5$ alkyl;

said siloxane having at least two hydrolyzable groups is a siloxane of formula 2:

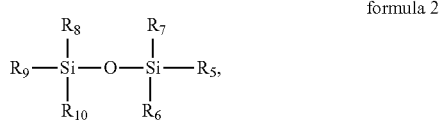

formula 2 wherein, at least two of $R_5$, $R_6$, $R_7$, $R_8$, $R_9$ and $R_{10}$ are each independently $-OR_A$ or $-OCOR_{15}$, at most four of $R_5$, $R_6$, $R_7$, $R_8$, $R_9$ and $R_{10}$ are each independently —$R_{16}$, $R_{14}$ and $R_{15}$ are each independently a linear or branched $C_1$-$C_5$ alkyl, and $R_{16}$ is a linear or branched $C_1$-$C_5$ alkyl.

12. The process according to claim 11, wherein said silane having at least two hydrolyzable groups is one or more selected from the group consisting of tetramethoxyl silane, tetraethoxy silane, methyltrimethoxy silane, ethyltrimethoxy silane, dimethyldimethoxy silane, diethyldimethoxy silane, methyltriethoxy silane, dimethyldiethoxysilane, methyl metasilicate and ethyl metasilicate; and said siloxane having at least two hydrolyzable groups is 1,3-dimethoxy-1,1,3,3-tetramethyl disiloxane and/or 1,3-diethoxy-1,1,3,3-tetramethyl disiloxane.

13. The process according to claim 7, wherein said binder source further comprises a silica sol, and the weight ratio of the silica in the silica sol to the silane and/or siloxane having at least two hydrolyzable groups is 1:(0.02-1), both calculated in silica.

14. The process according to claim 7, wherein said base is one or more selected from the group consisting of sodium hydroxide, potassium hydroxide, tetramethyl ammonium hydroxide and tetraethyl ammonium hydroxide, the concentration of the aqueous base solution is 0.1-10 mol %, and the weight ratio of the aqueous base solution to the shaped article is (0.5-5):1.

15. The process according to claim 7, wherein the conditions for thermal treatment comprise: a temperature of 60-120 degrees C., and a duration of 2-15 hours; and the conditions for calcination comprise: a temperature of 300-600 degrees C., and a duration of 5-15 hours.

16. A process for epoxidising an olefin, comprising contacting the olefin with hydrogen peroxide in a solvent in the presence of a catalyst, characterized in that said catalyst is the catalyst according to claim 1.

17. The process according to claim 16, wherein said olefin is propylene.

18. The process according to claim 16, wherein the conditions for contact comprises: the molar ratio of solvent:olefin:hydrogen peroxide is (4-15):(0.5-5):1, the contact temperature is 30-90 degrees C., the pressure is 0.5-4.5 MPa, the liquid hourly space velocity is 0.1-7 $h^{-1}$, and the pH of the reaction system is 5-8.

* * * * *